United States Patent [19]

Cho et al.

[11] Patent Number: 4,681,092
[45] Date of Patent: Jul. 21, 1987

[54] BALLOON CATHETER WRAPPING APPARATUS

[75] Inventors: George E. S. Cho, Natick; Stephen B. Kessler, Gloucester, both of Mass.

[73] Assignee: Kontron Inc., Everett, Mass.

[21] Appl. No.: 736,598

[22] Filed: May 21, 1985

[51] Int. Cl.$^4$ .................... A61B 19/00; A61M 25/00
[52] U.S. Cl. ................................. 128/1 D; 128/344; 604/96; 242/100.1
[58] Field of Search ............... 128/1 D, 344; 604/93, 604/96–100, 103, 104, 108; 242/86.1, 100.1

[56] References Cited

U.S. PATENT DOCUMENTS

| | | | |
|---|---|---|---|
| 2,815,180 | 12/1957 | Pratt | 242/86.1 |
| 2,824,705 | 2/1958 | Bowman | 242/75.4 |
| 2,904,272 | 9/1959 | Barrett | 242/54 A |
| 3,273,813 | 9/1966 | George | 242/54 A |
| 4,261,339 | 4/1981 | Wolvek et al. | |
| 4,362,150 | 12/1982 | Lombardi et al. | |
| 4,422,447 | 12/1983 | Schiff | 128/1 D |
| 4,444,186 | 4/1984 | Wolvek et al. | |
| 4,531,512 | 7/1985 | Wolvek et al. | 128/344 |
| 4,540,404 | 9/1985 | Wolvek | 128/1 D |
| 4,576,142 | 3/1986 | Schiff | |

OTHER PUBLICATIONS

Aries Medical Brochure (0385SP7.5M).
Aries Medical Balloon Tray Cover Sheet.
Aries Medical Percutaneous Intra-Aortic Balloon Package Insert (Revision 27) (108-0006).
SMEC "Sidewinder" Percutaneous Intra-Aortic Balloon Instructions (Jan. 8, 1985).
Datascope "Percor" Instructions (1980).

Primary Examiner—Stephen C. Pellegrino
Attorney, Agent, or Firm—Jon S. Saxe; Bernard S. Leon; George W. Johnston

[57] ABSTRACT

An apparatus for wrapping a balloon catheter such as an intra-aortic balloon catheter is disclosed. The wrapping apparatus comprises a housing having a channel which receives the balloon membrane of the intra-aortic balloon. The wrapping apparatus also includes a clutching means located in the channel for exerting a predetermined pressure on the balloon membrane to enable the balloon membrane to be wrapped as the wrapping apparatus is rotated relative to the balloon catheter. The clutching means also permits relatively free rotation of the balloon membrane within the wrapping apparatus after the balloon membrane has been wrapped.

The clutching means can include a shoe and a biasing means for biasing the shoe towards the balloon membrane with a predetermined pressure while the balloon membrane is being wrapped, yet enable the balloon membrane to rotate relatively freely within the wrapping apparatus after the balloon membrane has been wrapped to a predetermined degree.

The clutching means, alternatively, can include flexible vanes projecting inwardly within the channel such that the vanes contact the balloon membrane during wrapping and provide a predetermined pressure onto the balloon membrane which aids in wrapping yet permits the wrapped balloon membrane to rotate relatively freely within the wrapping apparatus.

36 Claims, 10 Drawing Figures

BALLOON CATHETER WRAPPING APPARATUS

BACKGROUND OF THE INVENTION

1. Field of the Invention

This invention relates to balloon catheters such as intra-aortic balloon catheters and pulmonary arterial balloon catheters. More particularly, the invention concerns an apparatus for wrapping a balloon catheter before the catheter is inserted into a patient. More specifically, the invention is directed to improved wrapping of intra-aortic balloon catheters.

2. Background Description

The use of balloon catheters in medicine is known. One of these balloon catheters is an intra-aortic balloon catheter.

An intra-aortic balloon catheter is utilized in balloon pumping and consists primarily of two segments: the balloon chamber or balloon, and the catheter tube. The catheter tube is a long thin hollow flexible tube, one end of which is fed into an artery of a patient and the other end of which remains outside the body. The balloon, which is sausage shaped, consists of a membrane attached to the end (distal) of the catheter tube that goes into the body. The end that remains outside the body (proximal) is equipped for connection to an external pump console. The console pumps gas, usually helium, through the catheter tube into the balloon.

The balloon membrane of an intra-aortic balloon catheter is not distensible. It does not stretch or contract but has a constant surface area irrespective of whether it is in its inflated or collapsed state.

In use, the balloon of the device is maneuvered by a physician so that it is positioned in the descending aorta, the major artery leading from the left ventricle of the heart to the other organs of the body. It is normally inserted into the body, however, through the femoral artery, which is located in the groin area of the thigh. From there, by pushing on the catheter tube itself, the physician can feed the balloon up through the arterial system until it reaches the aorta.

The balloon is then inflated and deflated again and again, out of phase with the natural pumping action of the heart. That is, immediately after the heart relaxes following a pump cycle, the balloon is inflated and just before the heart begins the next pumping action the balloon is deflated. This process is often called "counterpulsation."

The timing of the inflate/deflate cycle is controlled by the patient's electro-cardiogram or arterial blood pressure so that it is properly synchronized to the patient's natural heart rhythm. When the balloon is inflated, it forces blood out of the portion of the aorta where the balloon is located. In so doing, the inflation of the balloon causes a second pumping action, supplementing the natural pumping action of the heart. In particular, it forces extra oxygen-containing blood through the coronary arteries, thereby providing additional nourishment to the heart. Thereafter, when the balloon is deflated, the pressure in the aorta is lowered. Since there is then much less back pressure against which the heart must pump, the exertion of the heart muscle during the next pumping cycle is substantially reduced.

The intra-aortic balloon catheter is a temporary assist device, typically being left in the patient for about three days. It is frequently used after open-heart surgery to help wean a patient off a heart-lung machine. It is often used for patients suffering from cardiogenic shock, myocardial infraction and acute angina pectoris and is frequently used to sustain patients who might not otherwise be able to sustain themselves until permanent treatment can be affected.

The original intra-aortic balloon catheters were inserted by surgeons via a surgical procedure. The femoral artery was surgically exposed by making an incision in the groin. A second incision then was made in the artery, a graft was sewn in and the IAB inserted. Removal of the device requires surgery as well.

In surgical balloon catheters, the catheter tube itself ran the entire length of the balloon. In other words, the far (distal) end of the balloon was fixedly secured to the far end of the catheter tube and the near (proximal) end of the balloon was also fixedly secured to the catheter tube.

Today most intra-aortic balloons are inserted by cardiologist without the need for surgery. These intra-aortic balloon catheters are inserted by puncturing the artery with a needle instead of using a surgical incision. This procedure is called a percutaneous insertion. See Seldinger, *Catheter Replacement of the Needle in Percutaneous Arteriography*, Acta Radiol (Stockholm, Sweden), 39:368 (1953).

In percutaneous insertion, the patient is given a local anesthetic, after which a small incision is made in the skin over the femoral artery. A hypodermic needle then is used to puncture the femoral artery. The needle is replaced by a guide wire, over which is inserted a sheath. The percutaneous intra-aortic balloon catheter is introduced into the artery through the sheath.

The smaller the diameter or profile of the balloon catheter as it was being inserted into the femoral artery and being fed up into the aorta, the better. Making this entering profile small, however, has presented difficulties because the non-distensible balloon membrane does not contract when deflated.

Since the membrane of an intra-aortic balloon does not contract, some other methods were employed to make the entering profile as small as possible. With surgical intra-aortic balloons this was accomplished by bunching or wrapping the balloon membrane around the catheter tube within it. Because the catheter tube was within the balloon, however, no matter how tightly bunched the balloon could not be made any smaller than the tube itself.

In the early percutaneous intra-aortic balloon catheters, the profile of the balloon was further reduced by instead of attaching both ends of the balloon to the catheter tube, attaching only the proximal end of the balloon to it. Then a very thin rod or support member ran from the tip of the balloon through the balloon and terminated in the catheter tube.

The support member also was rotatably coupled to the catheter tube at the proximal end of the balloon so that the other end of the balloon could be twisted relative to the proximal end. By permitting the support member to rotate, it was possible, after evacuating air from the balloon to twist the balloon membrane into a spiral wrap about the support member.

Because the support member was much thinner than the catheter tube when the balloon was wrapped about the support member, it thus was made to have a diameter as small as that of the catheter tube. Since the physician guided the wrapped balloon catheter up to the aorta by pushing on the catheter tube, a disc shaped keeper preventing the support member from sliding or telescoping into the catheter tube was added, thereby permitting the pushing force to be transmitted from the catheter tube through the support member and to the balloon tip.

Certain difficulties were experienced with these early percutaneous intra-aortic balloon catheters. Since the balloon was wrapped after placing a vacuum on the balloon catheter and manually rotating the support member, the resulting spiral on the balloon tended to be uneven and non uniform. Often the balloon was over-wrapped by rotating excessively thus inducing torsional stress and fatigue on the balloon and creating a potential for the balloon to rupture in the patient during subsequent balloon inflation and deflation. Moreover, the early percutaneous intra-aortic balloon catheters were unwapped in the aorta of the patient by removing the vacuum previously placed on the balloon catheter. Due to the characteristics of the balloon material this allegedly permitted the balloon and its attached support member to unwind and return to their original unwrapped condition. There, however, was no accurate way to make certain that the balloon fully unwrapped in the aorta. Should the balloon not unwrap fully, proper counter-pulsation could not be achieved. The balloon catheter would have to be removed and a new balloon catheter inserted.

In later percutaneous intra-aortic balloon catheters, inter alia, the support member was completely modified from the early percutaneous devices so that it ran from the balloon tip, through the balloon and catheter tube and terminated in a rotatable wrap handle. By rotating the wrap handle, torsional forces were transmitted to the attached support member which in turn caused rotation of the balloon about the support member thereby reducing the balloon profile. The wrap handle included stops which prevented rotation of the handle and the attached support member by more than a predetermined number of rotations in either rotational direction. When the wrap handle was fully rotated in one direction and contacted a stop, the balloon would be completely wrapped but when fully rotated in the opposite direction until it contacted the other stop, the balloon would be completely wrapped. The wrap handle of these latter percutaneous intra-aortic balloon catheters provided positive controlled wrapping and unwrapping of the balloon from outside the patient. The use of the wrap handle eliminated the problems associated with the early percutaneous intra-aortic balloon catheters.

The present invention constitutes a further improvement in the technique of wrapping an intra-aortic balloon catheter. With the present invention, a wrap handle is no longer necessary to achieve positive controlled wrapping and unwrapping yet the problems associated with the early percutaneous balloon catheters not having wrap handles still are avoided.

SUMMARY OF THE INVENTION

This invention relates to an apparatus for wrapping a balloon catheter such as an intra-aortic balloon catheter.

The wrapping apparatus comprises a housing having at least one channel which receives the balloon membrane of the intra-aortic balloon catheter. The wrapping apparatus also includes a clutching means located in the channel for exerting a predetermined pressure on the balloon membrane to enable the balloon membrane to be wrapped as the wrapping apparatus is rotated relative to the balloon catheter. The clutching means also permits relatively free rotation of the balloon membrane within the wrapping apparatus after the balloon membrane has been wrapped. Thus, the clutching means in the wrapping apparatus avoids the potential of over-wrapping the balloon membrane.

The clutching means can include a shoe and biasing means for biasing the shoe towards the balloon membrane with a predetermined pressure while the balloon membrane is being wrapped, yet enable the balloon membrane to rotate relatively freely or slip within the wrapping apparatus after the balloon membrane has been wrapped by a predetermined degree.

The clutching means, alternatively, can include at least one flexible vane projecting within the channel such that the vane contacts the balloon membrane during wrapping and provides predetermined pressure onto the balloon membrane which aids in wrapping yet permits the wrapped balloon membrane to rotate relatively freely or slip within the wrapping apparatus.

In accordance with the invention, the intra-aortic balloon catheter is evacuated and inserted into the wrapping apparatus. The wrapping apparatus is rotated at least by a predetermined number of turns relative to the balloon membrane thereby wrapping the balloon membrane therein. The resulting wrap is uniform, tight and of a sufficient narrow profile to enable percutaneous insertion into the body of a patient.

The invention also concerns methods for wrapping balloon catheters by using the inventive wrapping apparatus.

The invention thus provides a safe, user-friendly, and simple method for wrapping intra-aortic balloon catheters, which avoids the problems associated with early percutaneous intra-aortic balloons, particularly problems of over-wrapping and unwrapping.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

The present invention concerns an apparatus for wrapping a balloon catheter before the catheter is inserted into the body of a patient. The wrapping apparatus preferrably is used for wrapping a percutaneous intra-aortic balloon catheter.

The wrapping apparatus includes a housing having a channel to receive at least a portion of the balloon membrane of the intra-aortic balloon catheter. The wrapping apparatus also includes a clutching means located in the channel for exerting a predetermined degree of pressure on the balloon membrane to aid in the wrapping of the balloon membrane as the wrapping apparatus is rotated relative to the balloon catheter yet permit relatively free rotation of the balloon membrane within the wrapping apparatus after the balloon membrane has been fully wrapped.

The housing can include an upper portion having a passage and a lower portion having a passage with the two housing portions secured together so that their passages form a channel for surrounding at least a portion of the balloon membrane.

In one embodiment, the clutching means comprises a shoe and a biasing means for biasing the shoe toward the balloon membrane with a predetermined pressure while the balloon membrane is being wrapped. The shoe has a first surface portion which is accurately configured to contact and conform with the diameter of the balloon membrane as the balloon membrane is being wrapped. The first surface portion of the shoe also can contain at least one rib which contacts the balloon membrane and aids in the wrapping of the balloon membrane as well as the ultimate removal of the wrapped balloon membrane from the wrapping apparatus.

In a preferred embodiment of the invention, the wrapping apparatus includes an elongated housing having a channel passing the length of the housing to receive and surround at least a portion of the unwrapped portion of the balloon. The wrapping apparatus also includes at least one flexible vane means projecting from the housing into the channel for exerting a predetermined pressure on the balloon membrane while the balloon membrane is being wrapped by rotating the wrapping apparatus relative to the balloon catheter. The vane means also is of sufficient flexibility to bend and thereby permit relatively free rotation of the wrapped balloon membrane within the wrapping apparatus after rotation of the wrapping apparatus by at least a predetermined number of revolutions.

In a further modification to the above embodiment, the vane means projects into the channel to divide the channel into at least two passages which communicate with each other. The leaves of the unwrapped balloon membrane occupy one of the passages while the central section of the balloon membrane occupies the other passage.

In a more preferred embodiment, the clutching means comprises at least two flexible and generally opposing vanes projecting tangentially inwardly within the channel such that the vanes contact the balloon membrane during wrapping of the balloon membrane and provide a predetermined pressure onto the balloon membrane which aids in its uniform wrapping yet permit the wrapped balloon membrane to rotate relatively freely within the wrapping apparatus. As the balloon membrane is wrapped and the resulting diameter of the balloon membrane increases, a portion of the vanes flexes radially outwardly from the balloon catheter while providing counter-pressure onto the balloon membrane which aids in the uniform wrapping of the balloon membrane.

In another preferred embodiment, there is at least one shoulder located within the channel and having a length sufficient to contact the fully wrapped balloon to maintain the balloon membrane at a predetermined position during wrapping and aid in the removal of the balloon membrane from the wrapping apparatus after the balloon membrane has been fully wrapped.

In accordance with another aspect of the present invention, methods are disclosed to wrap a balloon catheter by using the inventive wrapping apparatus. In one of such methods, the balloon membrane is evacuated and inserted into the channel of the wrapping apparatus. The wrapping apparatus is rotated relative to the balloon catheter to wrap the balloon membrane.

The preferred embodiments of the inventive wrapping apparatus and their use are further described hereinbelow with reference to FIGS. 1–10.

Figure 1:
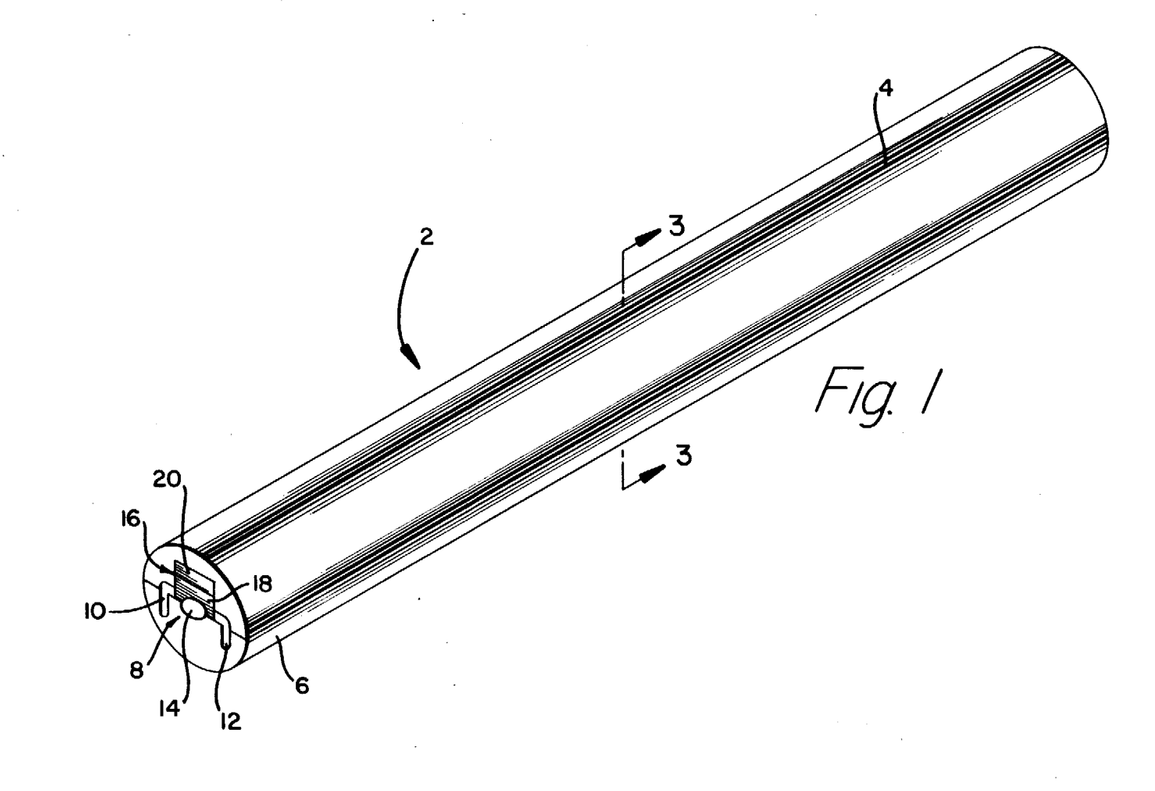
FIG. 1 is a perspective view of an intra-aortic balloon catheter wrapping apparatus of the present invention.
Figure 2:
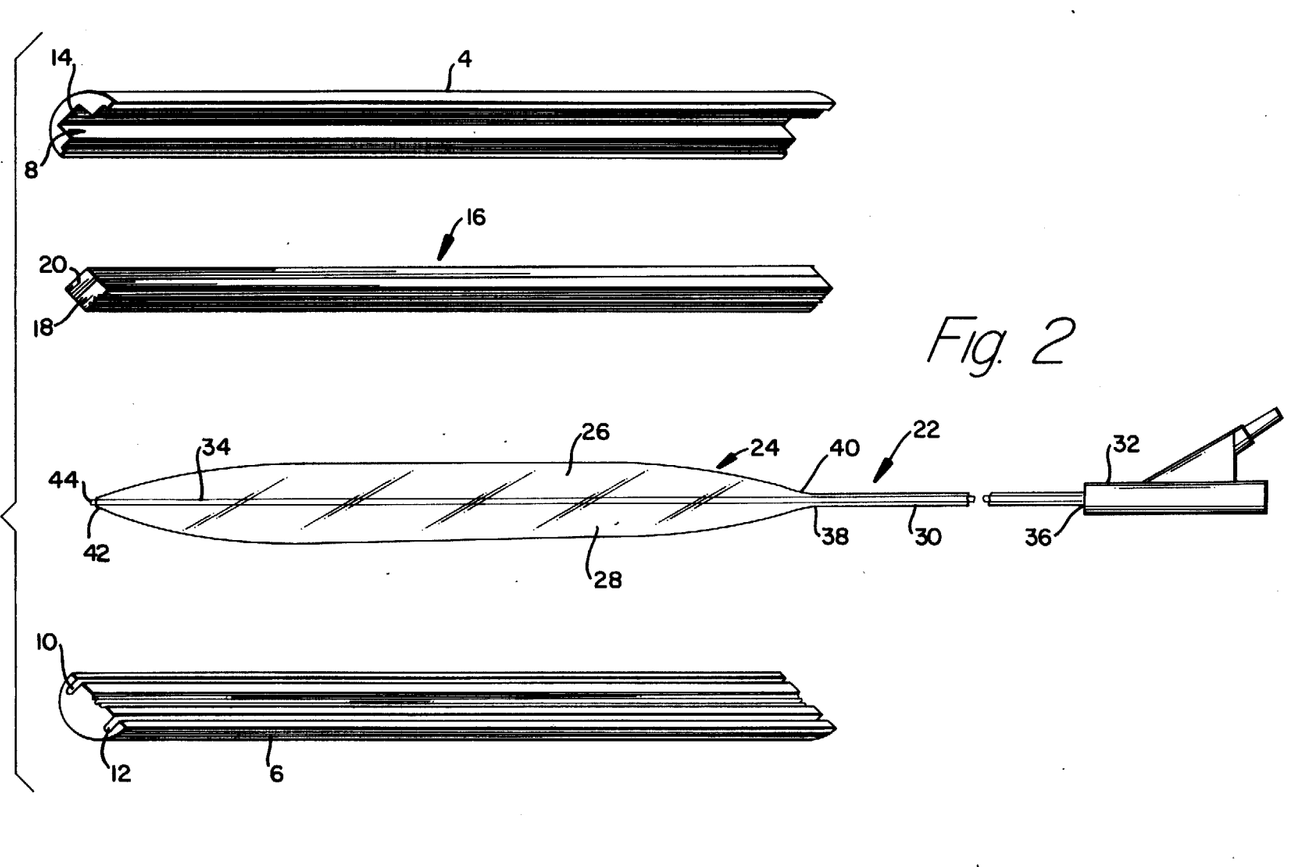
FIG. 2 is a perspective view of the various components of the wrapping apparatus of FIG. 1 and an intra-aortic balloon catheter.

FIGS. 1 and 2 illustrate an intra-aortic balloon catheter wrapping apparatus 2 of the present invention. Wrapping apparatus 2 includes an upper housing portion 4, a lower housing portion 6, a channel 8 with side passages 10 and 12 and a central passage 14, and clutching means 16 with a shoe 18 and biasing means 20.

Upper housing portion 4 is releasably secured to lower housing portion 6 thereby forming channel 8 therein. Channel 8 passes through the entire length of wrapping apparatus 2, and clutching means 16 is resiliently secured within central passage 14 of channel 8. In particular, biasing means 20, which for example consists of a foam rubber strip or a spring, is secured permanently to shoe 18, and the resulting clutching means is securely resiliently within central portion 14 of channel 8 to permit biased movement of clutching means 16 within said channel.

FIG. 2 also shows a representative unwrapped percutaneous intra-aortic balloon catheter 22 which can be wrapped by wrapping apparatus 2. Intra-aortic balloon catheter 22 includes balloon membrane 24 with side leaves 26 and 28, catheter tube 30, wye 32 and support member 34. Wye 32 is connected to proximal end 36 of catheter tube 30, and distal end 38 of catheter 30 is sealidly connected to proximal end 40 of balloon membrane 24. Distal end 42 of balloon membrane 24 is connected to tip 44 of support member 34. Support means 34 passes from tip 44 through balloon membrane 24, through catheter 30 and into wye 32. Support member 34 is fixedly secured to wye 32.

Intra-aortic balloon catheter 24 is evacuated and inserted into channel 8 of wrapping apparatus 2 such that its side leaves 26 and 28 are positioned within side passages 10 and 12, respectively. The positioning of unwrapped intra-aortic balloon catheter 22 in wrapping apparatus 2 can readily be seen in FIG. 3.

Figure 3:
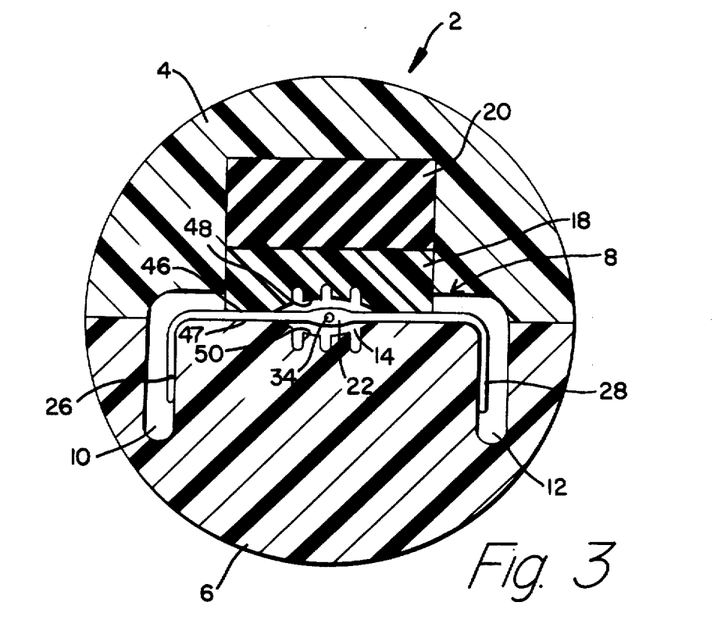
FIG. 3 is a cross-sectional view taken along lines 3—3 of FIG. 1, in which an intra-aortic balloon catheter is shown in an unwrapped configuration.

FIG. 3 illustrates a cross-sectional view of wrapping apparatus 2 with intra-aortic balloon catheter 22 positioned therein in an unwrapped configuration. Leaves 26 and 28 of intra-aortic balloon catheter 22 respectively are positioned within side passages 10 and 12 of channel 8. Shoe 18 presses upon such leaves due to the biasing forces exerted on it by biasing means 20. More particularly, shoe 18 includes a first surface 46 having an arcuate center surface 48. Surface 46 is in frictional contact with at least portions of leaves 26 and 28 respectively and is opposed by surface 47 of channels 10 and 12. Center section 48 has a sawtoothed or ribbed configuration so as to aid in wrapping and in sliding intra-aortic balloon membrane 24 in and out of wrapping apparatus 2. Central passage 14 of channel 8 also includes a lower central surface 50 of central portion 14 which has an arcuate sawtoothed or ribbed configuration to aid in wrapping and in sliding balloon membrane 24 in and out of wrapping apparatus 2.

The sawtooth configuration of surface portion 48 and 50 aids in the uniformness and tightness of the wrap of balloon membrane 24 by adding to the frictional forces being applied to balloon membrane 24. Sawtooth arcuate surfaces 48 and 50 also aid in the ease of removal of the fully wrapped intra-aortic balloon catheter 22 from wrapping apparatus 2. With these surfaces, balloon membrane 24 can be more easily advanced along the length of wrapping apparatus 2 because the ribbed shaped surfaces 48 and 50 decrease contact area to thereby reduce surface friction for sliding thereon along the length of wrapping apparatus 2 in the longitudinal direction.

After balloon membrane 24 with side leaves 26 and 28 has been disposed within and surrounded by channel 8 of wrapping apparatus 2, the wrapping apparatus is rotated around the longitudinal axis of intra-aortic balloon catheter 22 (i.e., about support member 34) by at least a predetermined number of rotations while the balloon catheter is held in a relaively stable position. As wrapping apparatus 2 is rotated about balloon membrane 24, torque is transmitted to balloon membrane 24 for twisting leaves 26 and 28 about themselves and support member 34. As the leaves wrap about support member 34, they thus advance along side passages 10 and 12 toward central passage 14 and rotate about each other so as to form a spiral. Frictional drag forces are exerted on advancing leaves 26, 28 by first face surface 46 of shoe 18 and opposing surface 47 which creates an outwardly directed tension along the leaves. This assures a tight uniform wrap.

As the spirally advancing leaves increase in diameter, they contact arcuate surfaces 48 and 50 creating frictional drag forces therebetween. These drag forces are sufficient to maintain tangentially-directed tension along the spiralling leaves to assure their tight, uniform wrapping.

With the diameter of the spiralling leaves increasing, shoe 18 is pushed away from central passage 14 toward biasing means 20. In turn, biasing means 20 exerts a counter-pressure on shoe 18 sufficient to maintain frictional contact between arcuate surface 48 of shoe 18 and spiralling leaves 26 and 28. This surface contact is sufficient to maintain tension on the spiralling leaves to assure a tight, uniform wrap. In view of the preselected pressure exerted by biasing means 20 into shoe 18 which in turn is transmitted onto leaves 26 and 28 of balloon membrane 24, controlled wrapping of the balloon membrane 24 within central passage 14 is achieved. After a certain number of rotations, leaves 26 and 28 are fully wrapped around support member 34 and the above described tension on the spiral is sufficient to overcome the drag forces. Additional rotation of wrapping apparatus 2, thus, does not provide significantly additional wrapping of balloon membrane 24.

Figure 4:
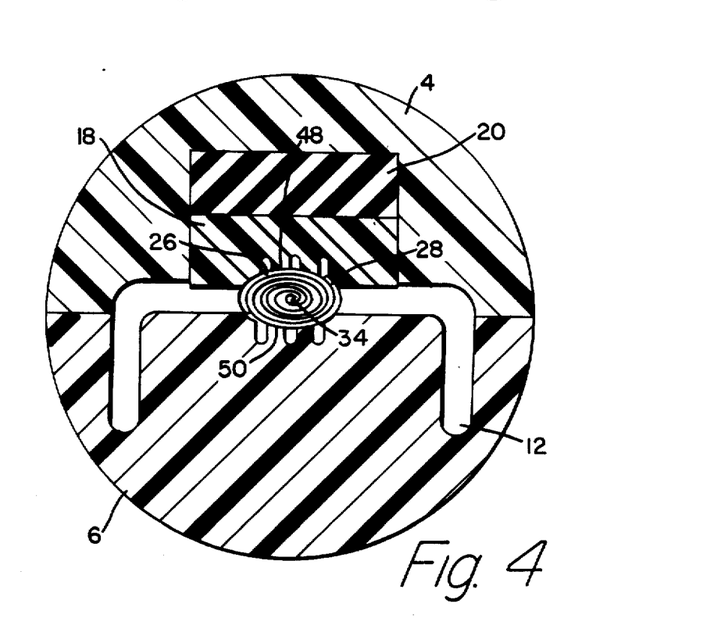
FIG. 4 is the cross-sectional view as shown in FIG. 3 in which the intra-aortic balloon catheter is shown in a fully wrapped configuration.

FIG. 4 illustrates fully wrapped balloon membrane 24 within wrapping apparatus 2. As can be seen, leaves 26 and 28 are fully wrapped around membrane 34 in a spiral fashion and shoe 18 has advanced upwardly away from lower housing portion 6 and support member 34 and toward biasing means 20. The thickness of biasing means 20 has decreased to compensate for the advance of shoe 18 toward biasing means 20.

As seen in FIG. 4, the outer diameter of the wrapped balloon membrane 24 has a surface configuration which is substantially similar to that of arcuately-shaped center section 48 of first surface 46 of shoe 18.

As seen in FIG. 4, after leaves 28 and 26 are fully wrapped about support member 34 a friction clutch like action results wherein wrapping apparatus 2 can rotate substantially freely about fully wrapped balloon membrane 24 and balloon membrane 24 does not achieve any significant increase in wrapping. The balloon catheter thus cannot be over-wrapped and therefore the problem of balloon ruptures and tearing due to wrapping too tightly is avoided.

In the above described embodiment, wrapping apparatus 2 including upper housing portion 4 and lower housing portion 6, and shoe 18 preferably is made of machinable, injection moldable or extrudable polymers (e.g. polyethylene, polyproplene, polycarbonate or polyacetals). Biasing means 20 preferably is made of a foam rubber or springs secured to shoe 18. Upper and lower housing portions 4 and 6 preferably have a length of about 9¾ inches and a diameter of about ⅝ inches. The shoe is about ⅛ inches high and ⅜ inches wide.

The method for using wrapping apparatus 2 of the present invention is illustrated with reference to the drawings, particular FIGS. 1 through 6. The percutaneous insertion method, described in the backgound section of this patent, is preferred and will be described further hereinbelow in conjunction with the present invention.

Figure 5:
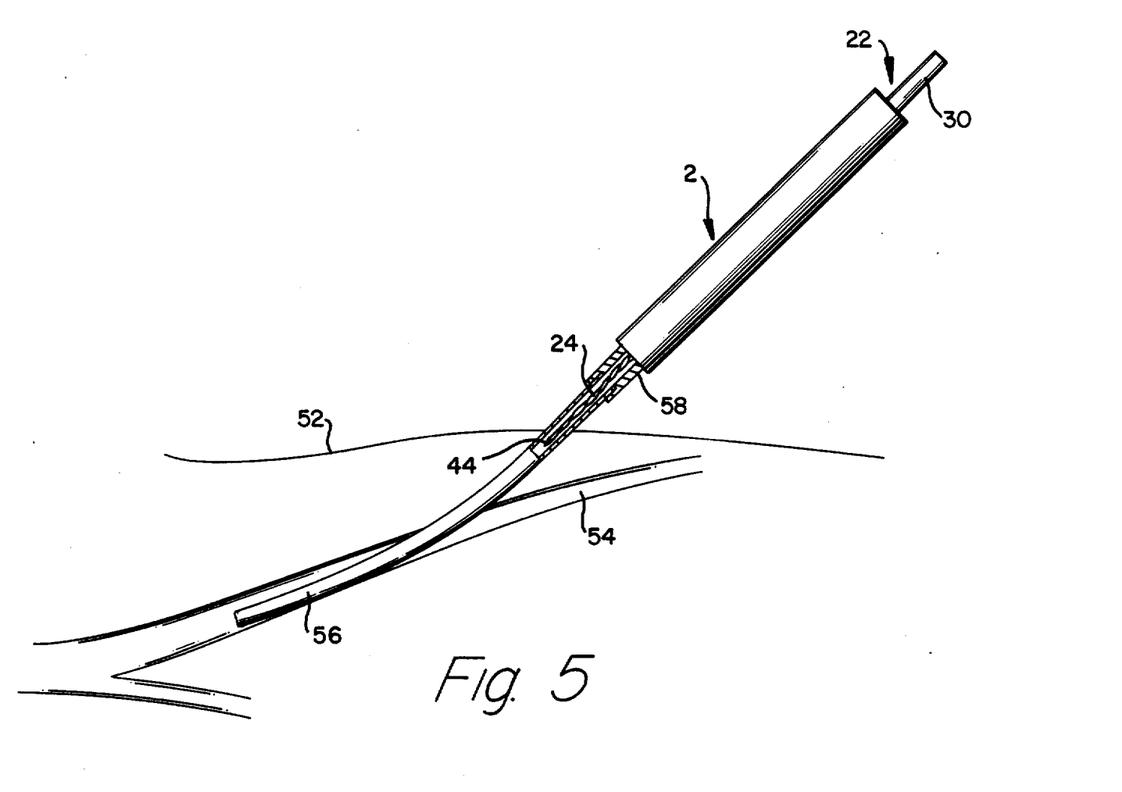
FIGS. 5 and 6, partly in cross section, illustrate the manner in which an intra-aortic balloon catheter wrapped by the wrapping apparatus of the present invention is inserted into the body of a patient.
Figure 6:
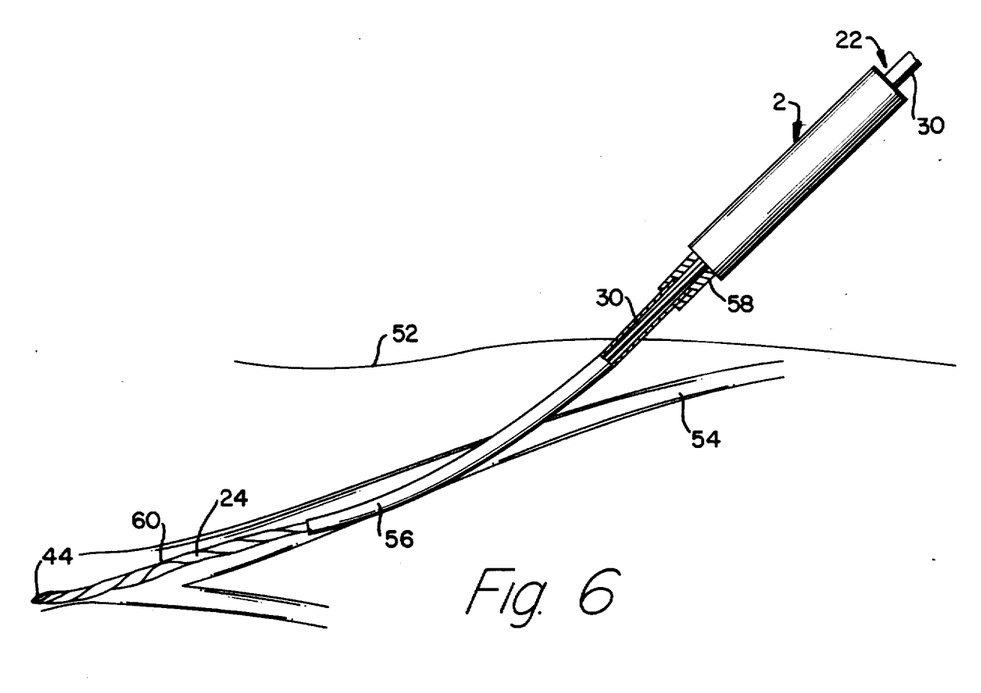

FIGS. 5 and 6 illustrate the percutaneous insertion technique for intra-aortic balloon catheter 22 wrapped with wrapping apparatus 2. In FIGS. 5 and 6 there is shown skin 52, femoral artery 54, sheath 56 with hub 58, balloon membrane 24, wrapping apparatus 2 and catheter tube 30. After the physician has inserted sheath 56 through skin 52 and into femoral artery 54, balloon membrane 2, is prepared for insertion into sheath 56. A vacuum is drawn on catheter 22 so that air is extracted from balloon membrane 24 and leaves 26 and 28 collapse to a relatively thin envelope.

Evacuated intra-aortic balloon membrane 24 then is inserted into and surrounded by wrapping apparatus 2 with leaves 26 and 28 positioned respectively within side passages 10 and 12 of channel 8 and support member 24 positioned within central passsage 14. The physician then rotates wrapping apparatus 2 about intra-aortic balloon catheter 22 such that balloon membrane 24 tightly rotates about support member 34 and obtains the wrapped configuration described above and illustrated in FIG. 4. After rotating wrapping apparatus 2, for example approximately 5 times, balloon membrane 24 is fully wrapped.

With wrapping apparatus 2 remaining around the wrapped balloon catheter 22, fully wrapped balloon membrane 24 is positioned adjacent to free end of hub 58 of sheath 56, and tip 44 of balloon catheter 22 is advanced through hub 58 into sheath 56. As seen in FIG. 5, wrapping apparatus 2 contacts the free end of hub 58, and tip 44 together with its balloon membrane 24 advances through sheath 56 and into femoral artery 54.

As wrapped balloon membrane 24, exits from wrapping apparatus 2 and advances into sheath 56, catheter 30, attached to balloon membrane 24, enters the other end of wrapping apparatus 2.

After the wrapped balloon membrane 24 has completely advanced into sheath 56, wrapping apparatus 2 surrounds catheter tube 30 of intra-aortic balloon catheter 22. Wrapping apparatus 2 then slid from sheath 56 and toward the physician. Wrapping apparatus 2 then can be taken apart by separating upper housing portion 4 from lower housing portion 6.

Wrapped intra-aortic balloon catheter 22 is advanced through sheath 56, through femoral artery 54 and into the aorta at a location where intra-aortic balloon catheters are normally positioned.

As seen in FIG. 6, the configuratin of wrapped balloon membrane 24 is such that the direction of the spiral proceeds from the proximal and distal ends of balloon membrane 24 simultaneously toward its central portion 60. This can be seen in FIG. 6 by noticing the direction of the opposing spirals of balloon membrane 24 which advance toward central portion 60 of balloon membrane 24.

After removing the vacuum from intra-aortic balloon catheter 22, wrapped balloon membrane 24 automatically fully unwraps due to the resiliency of the material. The unwrapping is quite simple since balloon membrane 24 merely unwinds around fixed support member 34, without support member 34 also having to rotate. In other words, balloon membrane 24 simply unfurls into a fully unwrapped balloon membrane which then can be inflated or deflated in accordance with standard intra-aortic balloon pumping practices.

Figure 7:
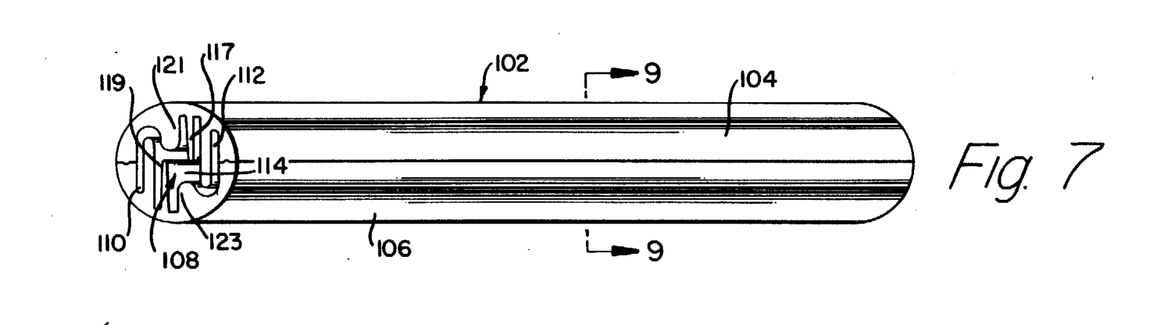
FIG. 7 is a perspective view of a more preferred embodiment of an intra-aortic balloon catheter wrapping apparatus of the present invention.
Figure 8:
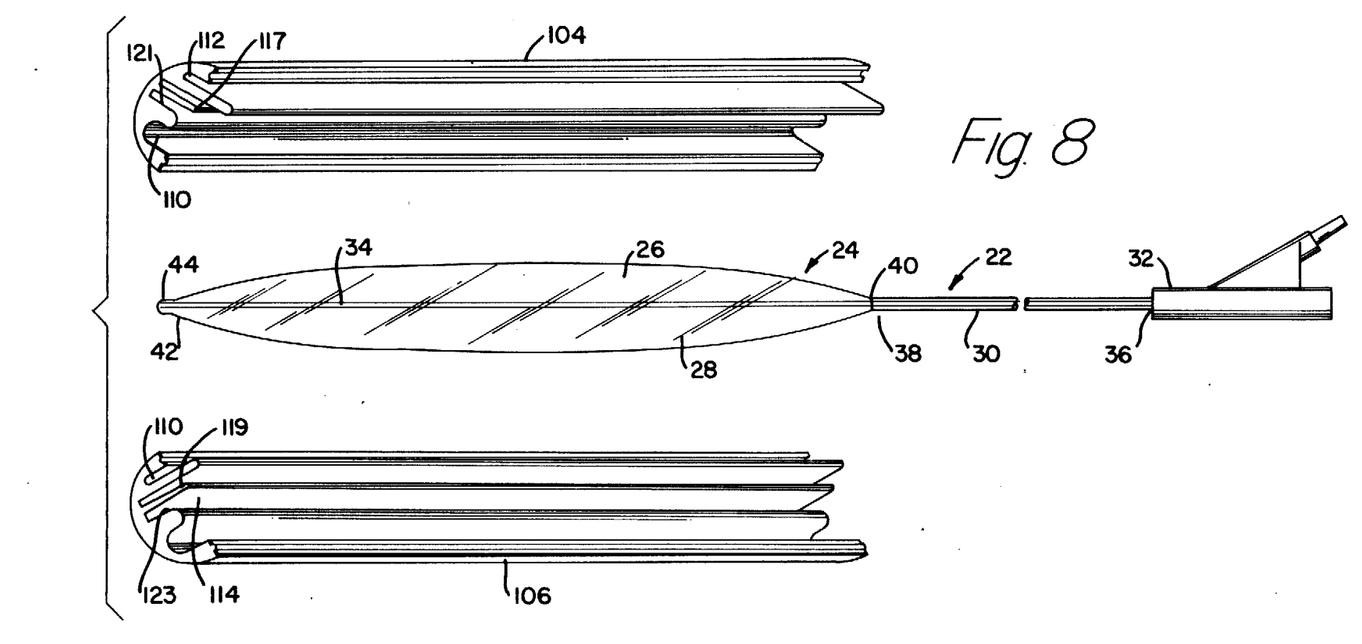
FIG. 8 is a perspective view of the various components of the wrapping apparatus of FIG. 7 and an intra-aortic balloon catheter.

FIGS. 7 and 8 illustrate another preferred embodiment of an intra-aortic balloon catheter wrapping apparatus of the present invention. There is shown a wrapping apparatus 102 which includes an upper housing portion 104, a lower housing portion 106, a channel 108 with side passages 110 and 112 and a central passage 114, and clutching means comprising flexible vanes 117 and 119. Upper housing portion 104 is secured releasably to lower housing portion 106 thereby forming channel 108 therein. Channel 108 passes through the entire length of wrapping apparatus 102, and clutching means, by way of vanes 117 and 119, projects into central passage 114 of channel 8 and passes the entire length of channel 108.

Vanes 117 and 119 are integrally formed as parts of upper housing portion 104 and lower housing portion 106, respectively. Such vanes 117 and 119 are configured and dimensioned to be resilient yet flexible so as to move toward or away from the center of the cross section of wrapping apparatus 102 within central passage 114. In FIGS. 7 and 8 there additionally is shown shoulders 121 and 123 which project into central passage 114 and run the entire length of wrapping apparatus 102.

FIG. 8 also shows a representative percutaneous intra-aortic balloon catheter 22 which is substantially identical to the catheter described with regard to FIG. 2.

Figure 9:
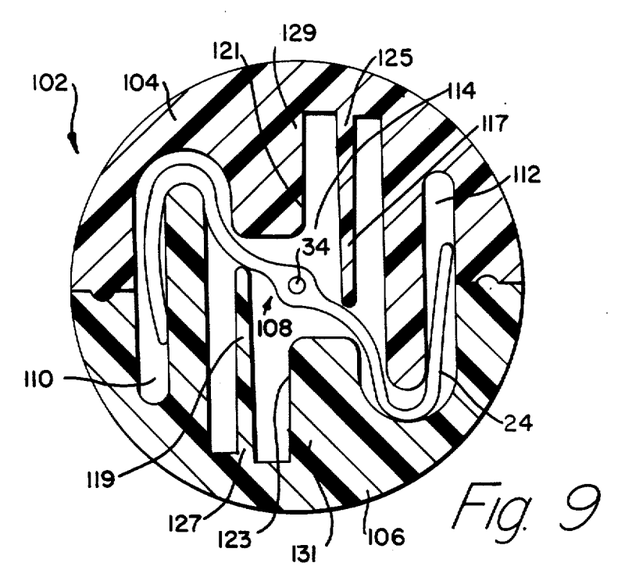
FIG. 9 is a cross-sectional view taken along lines 9—9 of FIG. 7 in which an intra-aortic balloon catheter is shown in an unwrapped configuration.

FIG. 9 illustrates a cross sectional view of wrapping apparatus 102 with intra-aortic balloon 22 positioned therein in an unwrapped state. Intra-aortic balloon catheter 22 is inserted into channel 108 of wrapping apparatus 102. Leaves 26 and 28 of intra-aortic balloon catheter 22 respectively are positioned within side passages 110 and 112 of channel 108.

Vane 117 projects from a point 125 generally adjacent the circumference of upper housing 104 into central passage 114 and in a direction generally tangential to the center of central passage 114. Similarly, vane 119 projects from a point 127 generally adjacent the circumference of lower housing portion 106 into central passage 114 and in a direction generally tangential to the center of central passage 114. Vanes 117 and 119 are substantially flexible and flex about points 125 and 127 respectively in a direction away from the cross sectional center of central passage 114.

Shoulder 121 projects from a point 129 adjacent the circumference of upper housing portion 104 into central passage 114 and in a direction toward the center of central passage 114. Similarly, shoulder 123 projects from a point 131 generally adjacent the circumference of lower housing portion 106 into central passage 114 in a direction generally toward the center of central passage 114. Shoulders 121 and 123 need not be flexible. They are used to centralize intra-aortic balloon member 24, and its support member 34, within the center of central passage 114. Shoulders 121 and 123 also aid in the sliding removal of fully wrapped balloon catheter 22 from wrapping apparatus 102.

Figure 10:
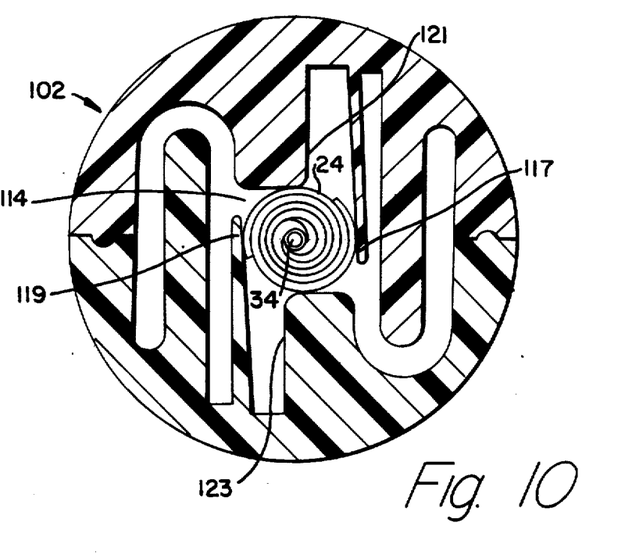
FIG. 10 is the cross-sectional view as shown in FIG. 9 in which the intra-aortic balloon catheter is shown in a fully wrapped configuration.

The functioning of vanes 117, 119 and shoulders 121 and 123 can be seen with reference to FIG. 10 and is comparable to the functioning of shoe 18 and biasing means 20 as described above. After evacuated balloon membrane 24 with side leaves 26 and 28 has been disposed within and surrounded by channed 108 of wrapping apparatus 102, and leaves 26 and 28 thereby are positioned within side passages 110 and 112 respectively, wrapping apparatus 102 is rotated about the longitudinal axis of intra-aortic balloon catheter 22 by at least a predetermined number of rotations as balloon catheter 22 is held in a relatively stable and fixed position. With reference to FIGS. 9 and 10, wrapping apparatus 102 preferrably is rotated in the counter clockwise direction.

As wrapping apparatus 102 is rotated about balloon membrane 24, torque is transmitted to balloon membrane 24 for twisting leaves 26 and 28 about themselves and support member 34 thus forming a spiral. As the leaves wrap about support member 34, they advance along side passages 110 and 112 toward central passage 114. Frictional drag forces on the side walls of channels 110 and 108 create an outwardly directed tension along leaves 26 and 28. This assures a tight uniform wrap. As the rotation of the wrapping apparatus 702 continues, the resulting spiral begins to increase in diameter and the spiral contacts the side of flexible vanes 117 and 119 forcing such vanes to move outwardly from the center of central passage 114. This maintains a frictional drag force on the spiral yet permits the diameter of wrapping balloon membrane 24 to increase in size.

Flexible vanes 117 and 119 generally pivot about points 125 and 127, respectively, but are of a configuration and dimension to provide firm control and drag pressure onto spiralling balloon membrane 24 to maintain a tight, uniform wrapping of the balloon membrane 24 as wrapping apparatus 102 rotates about intra-aortic balloon catheter 22. In view of their configuration, vanes 117 and 119 are biased such that the pressure on such vanes caused by the increasing diameter of such wrapping balloon membrane 24 creates a counter-pressure into balloon membrane 24 by such vanes. During the beginning of the wrapping process, vanes 117 and 119 thus contact balloon membrane 24 and continue to remain in contact for the remainder of the wrapping. The resulting frictional drag forces between the vanes and the spiral are sufficient to maintain tagentially-directed tension along the spiraling leaves to assure their tight, uniform wrapping. In view of the pressure exerted by vanes 117 and 119 onto the spiralling balloon membranes 24, controlled wrapping is achieved. After a certain number of rotations of wrapping apparatus 102, leaves 26 and 28 are fully wrapped around support membrane 34 and the above described tension on the spiral is sufficient to overcome the drag forces. Any additional rotation of the wrapping apparatus 102, thus, does not create significant additional wrapping of balloon membrane 24.

When balloon membrane 24 is fully wrapped about support member 34 as shown in FIG. 10, the balloon membrane generally is positioned between shoulders 121 and 123. Such shoulders aid in the centralizing of the wrapped balloon membrane 24 within central passage 114. They also aid in the sliding of wrapping apparatus 102 along the longitudinal axis of balloon membrane 24 during the removal of wrapping apparatus 102 from around wrapped balloon membrane 24 in the same manner that sawtoothed arcuate surfaces 48 and 50 of wrapping apparatus 2 and in removal of its balloon catheter.

As seen in FIG. 9 after balloon membrane 24 is fully wrapped, balloon membrane 24 is positioned between vanes 117 and 119 and shoulders 121 and 123. Since leaves 28 and 26 are fully wrapped about support member 34, a friction clutching action occurs wherein wrapping apparatus 102 fully continues to rotate or slip about fully wrapped balloon membrane 24 but no significant increase in wrapping occurs. Balloon membrane 24, thus, cannot be over-wrapped, which avoids the prior art problem of balloon ruptures and tearing due to wrapping too tightly.

In the above described embodiment, wrapping apparatus 102 including upper housing portion 104 and lower housing portion 106 preferably is made of machinable, injection moldable extrudable polymers (e.g. polyethylene, polypropylene polycarbonate or polyacetals. Preferably the mold for upper housing portion 104, including vane 117 and shoulder 121 integrally formed thereon, is identical to the mold for lower housing portion 106 with its vane 119 and shoulder 123 integrally formed thereon. Preferrably, upper and lower housing 104 and 106 are about 9¾ inches long and about ⅝ inches in diameter. The length and thickness of the vanes, channels and shoulders vary depending on the size of the balloon to be wrapped and the material selected for the wrapping apparatus. For a polyethylene wrapping apparatus used with a 12 French intra-aortic balloon catheter, the vanes are about 0.02 inches in thickness and 0.25 inches in height. Side passages of the channels are about 0.04 inches and shoulders are about 0.08 inches in thickness and 0.14 inches in height.

The method of using wrapping apparatus 102 of the present invention is generally similar to that described above particularly with regard to FIGS. 5 and 6.

While the invention has been described in conjunction with certain embodiments, it is understood that various modifications and changes may be made without departing from the spirit and scope of the invention.

For example, shoe 18 and biasing means 20 of wrapping apparatus 2 can be an integral component consisting of one material which is biased toward leaves 26 and 28 of balloon membrane 24. Side passages 10 or 110 and 12 or 112 could have different configurations then as shown. For example, instead of the upside down U-shaped configuration as shown in FIGS. 3 and 4, side passages 10, 12 and 14 could have an modified S-shaped configuration or a spiral-shaped configuration. Instead of the modified N-shaped configuration as shown in FIGS. 9 and 10, channels 110 and 112 could have a U-shaped, a straight-line or S-shaped configuration.

Vanes 117 and 119 need not be an integral part of upper housing portion 104 or of lower housing portion 106 respectively but could be additional elements fixidly secured onto such housing portions. These vanes could be replaced by a biasing means and shoe similar to that described with regard to FIGS. 1 and 2 and those components could be secured within central passage 114 so as to contact the wrapping balloon membrane 24. Moreover, vanes 117 and 119 need not be positioned with their lengths tangential to the circumference of the spiralling balloon member 24. The length of the vanes could be positioned perpendicular (or anything in between) as long as they are sufficiently flexible to bend and permit spiralling of balloon membrane 24.

Moreover, while above discussions concerned rotation of wrapping apparatus 2 and 102 about intra-aortic balloon catheter 22 as the balloon catheter is held stationary, the wrapping apparatus could be held stationary and intra-aortic balloon catheter 22 rotated therein by a predetermined number of turns so as to wrap balloon membrane 24 within wrapping apparatus 2 or 102. Alternatively, the wrapping apparatus and the balloon could both be rotated in opposing directions.

It also is contemplated that the inventive wrapping apparatus be utilized with all major commercially available intra-aortic and other balloon catheters. These other catheters include pulmonary arterial balloon catheters and percutaneous translumenal angioplasty (e.g., coronary artery, renal artery and the like). To achieve a uniform, tight wrap, it is preferred that support member 34 of intra-aortic balloon catheter 22 be held relatively stationary in relation to the wrapping apparatus as balloon membrane 24 is wrapped. In other words, support member 34 should be made stationary by being non-rotatable with regard to balloon membrane 24. For example, the support member could be fixed to both ends of the balloon or the support member could continue through catheter 30 into wye 32 and be rigidly fixed therein to generally preclude its rotation.

The wrapping apparatus of the present invention also would work particularly well with the balloon catheter described in U.S. Pat. No. 4,362,150 to Lombardi et al. provided the wrapping handle shown therein is held or prevented from rotation as the present wrapping apparatus is rotated about the balloon membrane and it support member.

While the inventive wrapping apparatus preferably is utilized with percutaneous intra-aortic balloon catheters, the wrapping apparatus of the invention can be utilized with surgical balloons if a surgeon would desire a more uniformed wrap than was available prior to the present invention. In the surgical balloon, the support member 34 of FIG. 2 is merely replaced by an extension of catheter 30 into and through the entire length of the balloon and attached to tip 44 of the balloon catheter. The inventive wrapping apparatus would surround the balloon and wrap in the manner described above.

The inventive wrapping apparatus also can be utilized with a balloon catheter having an offset support member and at least one side leaf.

The inventive wrapping apparatus also need not have the cylindrical configurations as shown in the embodiments but can take on additional configurations such as for example, square, multi-sided, or ribbed. The inventive wrapping apparatus also can be used in conjunction with various shipping trays which have been utilized previously to hold an unwrapped intra-aortic balloon catheter during packaging and shipping to the physician. A tray also could be reconfigured to accept at least a portion of wrapping apparatus 2 and it could be shipped with an intra-aortic balloon catheter placed in an unwrapped state within the wrapping apparatus with the leaves of the balloon membrane positioned in the side passages of the wrapping apparatus. The tray could be configured to allow the doctor to rotate the wrapping apparatus within the tray while the tray itself generally secures the intra-aortic balloon catheter from rotation.

We claim:

1. An apparatus for wrapping a balloon catheter having a balloon membrane attached to a catheter tube comprising:
   (a) a housing having a channel to receive at least a portion of the balloon membrane of the balloon catheter; and
   (b) displaceable clutching means, at least a portion of which being located and positioned in the channel and functioning as follows: (i) during wrapping, engaging and being displaced by the balloon membrane to exert predetermined pressure on the balloon membrane to aid in the wrapping of the balloon membrane as the wrapping apparatus is rotated relative to the balloon catheter yet, and (ii) after wrapping, permitting relatively free rotation of the balloon membrane within the channel.

2. A wrapping apparatus for a balloon catheter having a catheter tube attached to a balloon membrane with a central section and two side leaves, comprising:
   (a) a housing having a central and two side passages, the central and two side passages being located in communication with each other, the central passage being configured to surround at least a portion of the central section of the balloon membrane and the side passages being configured to surround at least a portion of the respective side leaves of the balloon membrane; and
   (b) displaceable clutching means at least aa portion of which being located and positioned in said central passage and functioning as follows:
      (i) during wrapping, engaging the balloon membrane, being displaced by the wrapping balloon membrane, and exerting predetermined pressure on said balloon membrane along its length to aid in the wrapping of the balloon membrane as the wrapping apparatus is being rotated relative to the balloon catheter, and (ii) after a predetermined degree of wrapping, permitting relatively free rotation of the balloon membrane within the housing.

3. The wrapping apparatus of claim 2 wherein the clutching means comprises:
   (a) a shoe; and
   (b) biasing means for biasing the shoe toward the balloon membrane with a predetermined pressure while the balloon membrane is being wrapped.

4. The wrapping apparatus of claim 3 wherein the shoe runs the length of the central passage.

5. The wrapping apparatus of claim 3 wherein the shoe has a first surface portion which is accurately configured to contact the balloon membrane as the balloon membrane is wrapped.

6. The wrapping apparatus of claim 5 wherein the first surface portion of the shoe has at least one rib which contacts the balloon membrane.

7. The wrapping apparatus of claim 3 wherein the biasing means comprises a spring.

8. The wrapping apparatus of claim 3 wherein the biasing means comprises foam rubber.

9. The wrapping apparatus of claim 2 wherein the housing is approximately the same length as the balloon membrane.

10. The wrapping apparatus of claim 2 wherein the housing has two portions releasably secured to each other.

11. The wrapping apparatus of claim 10 wherein the first housing portion includes at least a portion of the central passage and the second housing portion includes at least a portion of the two side passages.

12. The wrapping apparatus of claim 10 wherein the second housing portion includes a fourth passage communicating with the other passages, said fourth passages being contiguous with the central passage such that said central and fourth passages surround the balloon membrane.

13. The wrapping apparatus of claim 12 wherein said fourth passage is arcuately configured to contact the balloon membrane during wrapping.

14. The wrapping apparatus of claim 13 wherein at least one rib is positioned along the length of the fourth passage to contact the balloon membrane.

15. The wrapping apparatus of claim 2 wherein the clutching means comprises at least one flexible vane means at least a portion of which is secured to the housing and projecting from the housing inwardly into the central passage to engage the balloon membrane and exert a predetermined pressure on the balloon membrane while wrapping yet permit relatively free rotation of the balloon membrane within the wrapping apparatus after the balloon membrane is wrapped to a predetermined amount of wrap.

16. The wrapping apparatus of claim 15 wherein the clutching means further comprises at least one shoulder means at least a portion of which projects within the central passage and has a length sufficient to maintain at least a portion of the balloon membrane at a predetermined position within the central passage.

17. The wrapping apparatus of claim 15 wherein there are at least two generally opposing shoulders projecting radially inwardly in the central passages, and of a length sufficient to centralize the balloon membrane therebetween during wrapping.

18. The wrapping apparatus of claim 17 wherein the shoulders run the length of the central passage.

19. The wrapping apparatus of claim 15 wherein the clutching means comprises at least two flexible vanes secured to the housing and projecting tangentially inwardly into the central passage so as to contact and provide predetermined pressure onto the balloon membrane during wrapping yet allow the balloon membrane relatively free rotation within the wrapping apparatus after the balloon membrane is wrapped to a predetermined degree.

20. The wrapping apparatus of claim 2 wherein the clutching means comprises at least two flexible and centrally opposing vanes secured to the housing and projecting from the housing inwardly into the central passage such that the vanes contact the balloon membrane during wrapping and provide a predetermined pressure onto the balloon membrane which aids in wrapping yet permits the wrapped balloon membrane to rotate relatively free within the wrapping apparatus.

21. The wrapping apparatus of claim 20 wherein at least a portion of each vane is configured to flex radially outwardly as the diameter of the balloon membrane increases during wrapping.

22. The wrapping apparatus of claim 21 wherein the vanes run the length of the central passage.

23. The wrapping apparatus of claim 20 wherein the vanes are integral with the housing.

24. The wrapping apparatus of claim 2 wherein the passages run the length of the housing.

25. A wrapping apparatus for an intra-aortic balloon catheter having a balloon membrane attached to a catheter tube, comprising:
 (a) a housing having:
  (i) an upper portion with a channel; and
  (ii) a lower portion with a channel;
  said upper portion and lower portions being releasably secured together so that the channels form a passage for surrounding at least a portion of the balloon membrane; and
 (b) displaceable clutching means, at least a portion of which being located and positioned in the passage and functioning as follows: (i) during wrapping, for contacting the wrapping balloon membrane, being displaced by the balloon membrane, and exerting predetermined pressure on the balloon membrane while the wrapping apparatus is rotated relative to the balloon catheter in an amount of rotations sufficient to wrap the balloon membrane about its longitudinal axis, and (ii) when the balloon membrane achieves a predetermined degree of wrapping, permitting relatively free rotation of the balloon membrane within the wrapping apparatus.

26. A wrapping apparatus for an intra-aortic balloon catheter having a catheter thus attached to a balloon membrane, comprising:
 (a) an elongated housing having a channel with a central passage and at least one side passage all passing the length of the housing to receive and surround at least a portion of the balloon membrane when the balloon membrane is in an unwrapped condition; and
 (b) at least one flexible vane means projecting from the housing inwardly into the channel and functioning as follows: (i) during wrapping, engaging the balloon membrane, being displaced by the wrapping balloon membrane, and exerting predetermined pressure on the balloon membrane as the wrapping apparatus is rotated relative to the balloon catheter to wrap the balloon membrane along its length, said flexible vane means being sufficiently flexible to bend as the diameter of the wrapping balloon membrane increases, and (ii) after rotating the wrapping apparatus at least by a predetermined member of revolutions, permitting relatively free rotation of the wrapped balloon membrane within the wrapping apparatus.

27. The wrapping apparatus of claim 26 wherein the clutching means further comprises at least two shoulders respectively projecting from the upper and lower housing portions into the central passage.

28. The wrapping apparatus of claim 27 wherein there are two side passages, and the central and two side passages run the length of the wrapping apparatus.

29. An apparatus for wrapping an intra-aortic balloon catheter having a catheter tube sealidly attached to a balloon membrane to permit fluidic communication therebetween, the balloon membrane having a central section and two side leaves, comprising:
 (a) a housing having:
  (i) an upper portion with a channel; and
  (ii) a lower portion with a channel;
  said upper portion and lower portions releasably secured together so that the channels form a central passage and at least one side passage, the central passage being located and configured to receive and surround the central section of the balloon membrane and the side passage being located and configured to receive and surround the side leaves of the balloon membrane; and
 (b) displaceable clutching means which includes at least two flexible vanes projecting respectively from the upper and lower portions of the housing inwardly into the central passage, and which functions: (i) during wrapping, to engage the balloon membrane and be displaced by the wrapping balloon membrane to provide predetermined pressure onto the balloon membrane as the wrapping apparatus is rotated relative to the balloon catheter to wrap the balloon membrane along its length yet, (ii) after wrapping the balloon membrane to a predetermined degree of wrapping, to allow the balloon membrane to rotate relatively freely within the wrapping apparatus.

30. An apparatus for wrapping a balloon catheter having a balloon membrane attached to a catheter tube, comprising:
 (a) a housing having a channel with at least two passages to receive portions of the balloon membrane; and
 (b) displaceable clutching means at least a portion of which being located and positioned in the channel and functioning as follows: (i) during wrapping, engaging the balloon membrane, being displaced by the wrapping balloon membrane, and exerting predetermined pressure on the balloon membrane to enable the balloon membrane to wrap as the wrapping apparatus is rotated relative to the balloon catheter, and (ii) after wrapping, permitting relatively free rotation of the balloon membrane within the channel.

31. An apparatus for wrapping a balloon catheter having a balloon membrane attached to a catheter tube, comprising:
 (a) a housing having a channel to receive at least a portion of the balloon membrane; and
 (b) displaceable clutching means having at least one vane means projecting from the housing inwardly into the channel to divide the channel into at least two passages and functioning as follows: (i) during wrapping, said vane means engaging the balloon membrane, being displaced by the wrapping balloon membrane, and exerting predetermined pressure onto the balloon membrane to aid in wrapping the balloon membrane while the wrapping apparatus is rotated relative to the balloon catheter, and (ii) after wrapping by a predetermined amount, said vane means being of sufficient flexibility to permit relatively free rotation of the balloon membrane within the channel.

32. A method for wrapping a balloon catheter having a catheter tube sealidly attached to a balloon membrane for fluidic communication therebetween said balloon membrane having a central section and two side leaves, the method comprising:
- (a) evacuating gas from the balloon catheter so as to collapse the balloon membrane;
- (b) inserting the balloon membrane into a wrapping apparatus having:
  - (i) a housing with a channel to receive at least a portion of the balloon membrane; and
  - (ii) displaceable clutching means at least a portion of which being located and positioned in the channel and functioning as follows: (1) during wrapping, engaging the balloon membrane, being displaced by the balloon membrane and exerting predetermined pressure on the balloon membrane to wrap the balloon membrane when the wrapping apparatus is rotated relative to the balloon catheter, and (2) after wrapping permitting relatively free rotation of the balloon membrane within the channel; and
- (c) rotating the wrapping apparatus relative to the balloon membrane by at least a predetermined number of revolutions to engage the clutching means with the balloon membrane and thereby wrap the balloon membrane.

33. The method of claim 32 wherein the channel of the wrapping apparatus has at least two passages, the side leaves of the balloon membrane being inserted into at least one of said passages and the central section of the balloon membrane being inserted into the other passage.

34. A method for wrapping a balloon catheter having a catheter tube sealidly attached to a balloon membrane for fluidic communication therebetween, said balloon membrane having a central section and two side leaves, the method comprising:
- (a) evacuating gas from the balloon catheter so as to collapse the balloon membrane;
- (b) inserting the balloon membrane into a wrapping apparatus having:
  - (i) a housing with a central and at least one side passage; and
  - (ii) flexible vane means projecting from the housing inwardly into the central passage for engaging the balloon membrane, being displaced by the wrapping balloon membrane, and exerting predetermined pressure on the balloon membrane, said balloon membrane being inserted into the wrapping apparatus such that at least one side passage surrounds at least one of the side leaves of the balloon membrane and the central passage surrounds the central section of the balloon membrane;
- (c) rotating the wrapping apparatus relative to the balloon catheter so as to wrap the balloon membrane; and
- (d) to the vane means, (i) during wrapping engaging the balloon membrane, and exerting a predetermined pressure on the balloon membrane as the wrapping apparatus is rotated relative thereto yet, said vane means being displaced by the wrapping balloon membrane, (ii) after wrapping, permitting relatively free rotation of the balloon membrane.

35. An apparatus for wrapping an intra-aortic balloon catheter having a catheter tube sealidly attached to a balloon membrane to permit fluidic communication therebetween and a stylet passing through the balloon membrane and at least into the catheter tube, comprising:
- (a) a housing having:
  - (i) an upper portion with a channel; and
  - (ii) a lower portion with a channel;
  said upper portion and lower portions being releasably secured together so that the channels form a central passage and at least one side passage, the central passage being located and configured to receive and surround the stylet and a portion of the balloon membrane and the side passage being located and configured to received and surround another portion of the balloon membrane; and
- (b) displaceable clutching means which includes at least two flexible vanes projecting respectively from the upper and lower portions of the housing inwardly into the central passage and which functions: (i) during wrapping, to engage the balloon member and be displaced by the balloon membrane to provide predetermined pressure onto the balloon membrane as the wrapping apparatus is rotated relative to the balloon catheter to wrap the balloon membrane about the stylet yet, (ii) after a predetermined degree of wrapping, to allow the balloon membrane to rotate relatively freely within the wrapping apparatus.

36. A method for wrapping a balloon catheter having a catheter tube sealidly attached to a balloon membrane to permit fluidic communication therebetween and a stylet passing through the balloon membrane and at least into the catheter tube, the method comprising:
- (a) evacuating gas from the balloon catheter so as to collapse the balloon membrane around the stylet;
- (b) inserting the balloon membrane into a wrapping apparatus having:
  - (i) a housing with a central and at least one side passage; and
  - (ii) flexible vane means projecting from the housing inwardly into the central passage for engaging the balloon membrane, being displaced by the wrapping balloon membrane and exerting predetermined pressure on the balloon membrane, said balloon membrane being inserted into the wrapping apparatus such that at least one side passage surrounds a portion of the balloon membrane and the central passage surrounds a portion of the balloon membrane about the stylet;
- (c) rotating the wrapping apparatus relative to the balloon catheter so as to wrap the balloon membrane about the stylet; and
- (d) by the vane means, (i) during wrapping, engaging the balloon membrane, and exerting a predetermined pressure on the balloon membrane as the wrapping apparatus is rotated relative thereto, said vane means being displaced by the wrapping balloon membrane, yet, (ii) after the balloon membrane has achieved a predetermined degree of wrapping, permitting relatively free rotation of the balloon membrane within the housing.

* * * * *

UNITED STATES PATENT AND TRADEMARK OFFICE
CERTIFICATE OF CORRECTION

PATENT NO. : 4,681,092

DATED : July 21, 1987

INVENTOR(S) : George E. S. Cho, Stephen B. Kessler

It is certified that error appears in the above-identified patent and that said Letters Patent is hereby corrected as shown below:

In Claim 2, line 46, "aa" should be --a--.

In Claim 5, line 68, the word "accurately" should be --arcuately--.

In Claim 20, line 66, the word "centrally" should be --generally--.

In Claim 26, line 39, the word "thus" should be --tube--.

Signed and Sealed this

Twenty-eighth Day of June, 1988

Attest:

DONALD J. QUIGG

Attesting Officer     Commissioner of Patents and Trademarks